United States Patent
Ueda et al.

(10) Patent No.: US 6,657,656 B1
(45) Date of Patent: Dec. 2, 2003

(54) MOUNT INSPECTION APPARATUS

(75) Inventors: Ryoichi Ueda, Ishikawa (JP); Tohru Kesyo, Ishikawa (JP); Yoshihisa Kajii, Ishikawa (JP); Koji Shimada, Ishikawa (JP)

(73) Assignee: Shibuya Kogyo Co., Ltd., Ishikawa (JP)

( * ) Notice: Subject to any disclaimer, the term of this patent is extended or adjusted under 35 U.S.C. 154(b) by 0 days.

(21) Appl. No.: 09/415,223

(22) Filed: Oct. 12, 1999

(30) Foreign Application Priority Data

Nov. 25, 1998 (JP) .............................. 10-350718

(51) Int. Cl.[7] .................... H04N 7/18; H04N 9/47; G06K 9/00
(52) U.S. Cl. ..................... 348/87; 348/126; 382/151
(58) Field of Search ...................... 348/86, 76, 87, 348/88, 90, 92, 95, 126; 382/145, 141, 147, 148, 150–152, 149; 702/113, 150; 356/237.1, 237.4, 602

(56) References Cited

U.S. PATENT DOCUMENTS

| | | | | |
|---|---|---|---|---|
| 5,465,152 A | * | 11/1995 | Bilodeau et al. ............. | 356/602 |
| 5,574,668 A | * | 11/1996 | Beaty .......................... | 702/150 |
| 5,574,801 A | * | 11/1996 | Collet-Beillon ............. | 382/150 |
| 6,151,406 A | * | 11/2000 | Chang et al. ................ | 382/147 |
| 6,396,942 B1 | * | 5/2002 | Chang et al. ................ | 382/141 |

* cited by examiner

Primary Examiner—Gims Philippe
(74) Attorney, Agent, or Firm—Sughrue Mion, PLLC

(57) ABSTRACT

A plurality of BGA packages are formed in a work, and alignment marks are put at least on the top and rearmost ones of the BGA packages. The top BGA package is stopped in an image pick-up area, and an alignment mark image and a ball image are picked up while relative movement between the work and a camera is started. Ball images of the second and the following BGA packages are picked up while the relative movement between the camera and the work is continued, the relative movement is stopped when a ball image of the last BGA package is picked up, and an alignment mark image of the rearmost BGA package is picked up after the relative movement is stopped. The positions of balls are calculated while the posture of the work as a whole is taken into consideration, and judgment is made as to whether the positions of balls are good or bad.

6 Claims, 4 Drawing Sheets

MOUNT INSPECTION APPARATUS

BACKGROUND OF THE INVENTION

1. Field of the Invention

The present invention relates to a mount inspection apparatus which is used after a BGA mount apparatus for absorbing balls become terminals on a circuit surfaces of BGA (ball grid array) packages so as to mount the balls on the BGA packages. The invention has been developed for the main purpose of providing an apparatus for detecting displacement of solder balls mounted on a plurality of BGA packages provided in a work.

The present application is based on Japanese Patent Application No. Hei. 10-350718, which is incorporated herein by reference.

2. Description of the Related Art

In the related art, in order to detect displacement of solder balls mounted on a work having a plurality of BGA packages, images of alignment marks and images of the solder balls were picked up, and the positions of the solder balls were confirmed with reference to the alignment marks. At that time, the alignment marks and the solder balls were seen in different ways according to a camera. Accordingly, the alignment images and the ball images were picked up while the relative movement between the camera and the BGA packages was stopped at every BGA package. It took much time for inspection because the camera was stopped at every BGA package to pick up images.

SUMMARY OF THE INVENTION

It is an object of the present invention to shorten the time of inspection by picking up images of alignment marks of only the top and rearmost ones of BGA packages, making judgement as to whether the positions of mounted balls are good or bad, and inspecting the displacements of the balls, that is, inspecting the number, position, size and so on of solder balls mounted on the BGA packages, without picking up images of alignment marks of BGA packages other than the top and rearmost packages on the basis of initially set BGA package data.

The present invention adopts the following steps in order to solve the foregoing problem. First, assume that, in a ball mount inspection apparatus, a plurality of BGA packages are formed in a work and alignment marks are put at least on the top and rearmost ones of the BGA packages.

Second, the top BGA package is stopped in an image pick-up area, an alignment mark image is picked up, and successively a ball image is picked up while relative movement between the work and a camera is started.

Third, ball images of the second and the following ones of the BGA packages are picked up while the relative movement between the camera and the work is continued, the relative movement is stopped when a ball image of the rearmost BGA package is picked up, and an alignment mark image of the rearmost BGA package is picked up after the relative movement is stopped.

Fourth, the posture of the work as a whole is obtained on the basis of the alignment marks of the top and rearmost BGA packages after the alignment mark image of the rearmost BGA package is picked up, the positions of balls mounted on the BGA packages are calculated while the above-mentioned posture is taken into consideration, and judgment is made as to whether the positions of the mounted balls are good or not.

Features and advantages of the invention will be evident from the following detailed description of the preferred embodiments described in conjunction with the attached drawings.

DETAILED DESCRIPTION OF THE PREFERRED EMBODIMENTS

Figure 2:
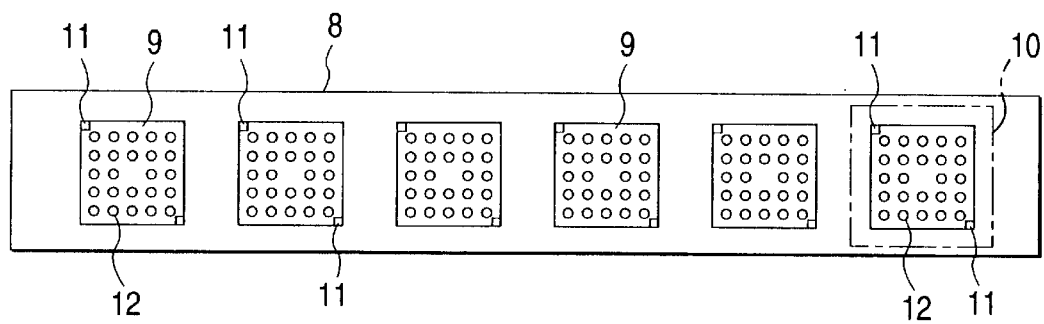
FIG. 2 shows an explanatory plan view of a BGA frame.

A mode for carrying out the invention will be described below with reference to an embodiment illustrated in the drawings. FIG. 2 is an explanatory plan view showing a BGA frame 8 used as a work in the present invention. A plurality of BGA packages 9 are formed in the BGA frame 8, and alignment marks 11 are put at least on the top one of the BGA packages 9 and the rearmost one of the BGA packages 9. The alignment mark 11 can be put by photo-etching outside of the wiring patterns in a shape of "+" mark. The alignment mark 11 can be made by the same manner and same material like copper as the wiring patterns. The BGA frame 8 in the illustrated embodiment has six BGA packages 9, and alignment marks 11 are put on the upper-left and lower-right diagonally opposite corner portions of each of the BGA packages 9. The reference numeral 12 in FIG. 2 represents solder balls which have been mounted on the BGA packages 9.

Figure 5:
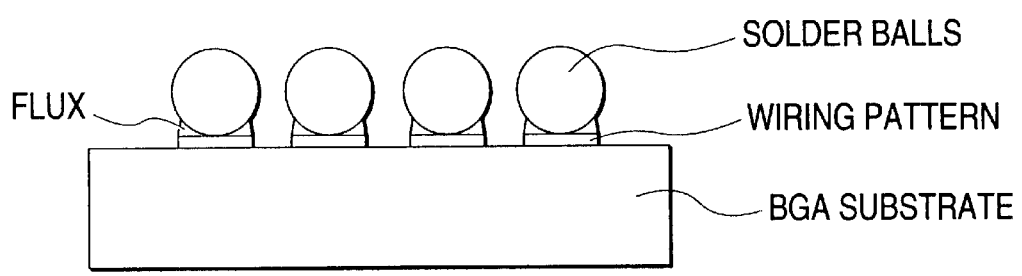
FIG. 5 is a schematic side view of the BGA package.

FIG. 5 is a schematic side view of the BGA package. A plurality of solder balls are mounted on the BGA substrate through the wiring patterns and flux.

Figure 1:
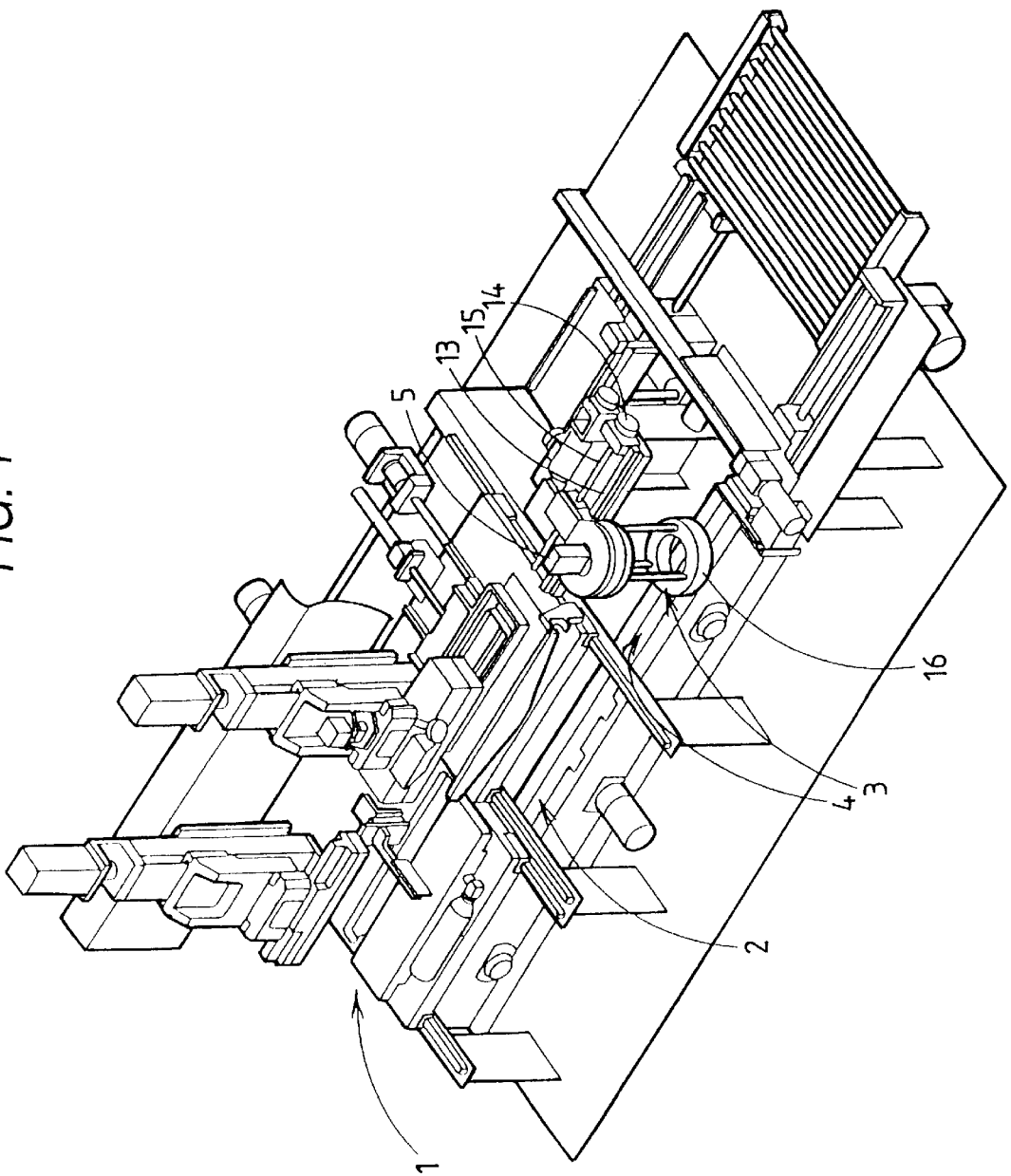
FIG. 1 shows a schematic view showing a mount apparatus as a whole.

A BGA solder ball mount apparatus for the BGA frame 8 will be described below with reference to a schematic view of FIG. 1. The BGA solder ball mount apparatus is constituted by a flux supply portion 1 for transferring flux to the BGA packages 9, a ball mount portion 2 for mounting solder balls 12 on the BGA packages 9, a mount inspection portion 3 for inspecting, through CCD camera 5, whether the ball mount has been performed properly or not, and a conveyor portion 4 for conveying the BGA frame 8 from the flux supply portion 1 to the ball mount portion 2 and the mount inspection portion 3.

The BGA frame 8 is supplied onto a conveyor (not shown) of the conveyor portion 4 by means of a not-shown carrier. The conveyor conveys the BGA frame 8 to the flux supply portion 1. After flux has been transferred to be BGA frame 8, the BGA frame 8 is conveyed to the ball mount portion 2. In the ball mount portion 2, the solder balls 12 are mounted on the respective BGA packages 9. After the solder balls 12 have been mounted, the BGA frame 8 is conveyed to the mount inspection portion 3.

In the mount inspection portion 3, inspection is performed as to whether the solder balls 12 have been mounted in predetermined positions of the BGA packages 9 properly. The mount inspection portion 3 is constituted by a CCD camera 5 for picking up images and an illuminator 16. The camera 5 and the illuminator 16 are integrated with each other and disposed on a running frame 13 disposed above the conveyor portion 4 so as to be able to be moved horizontally by a camera moving motor 14. The movement covers an area capable of detecting all the BGA packages 9 in the BGA frame 8.

An encoder is attached to the camera moving motor 14. A camera moving shaft 15 is rotated by the camera moving motor 14, and the motion of the CCD camera 5 moved by the motor is observed by the encoder. The number of pulses generated by the encoder is supplied to a high-speed counter, and the CCD camera 5 is triggered to pick up images in predetermined positions.

Figure 3:
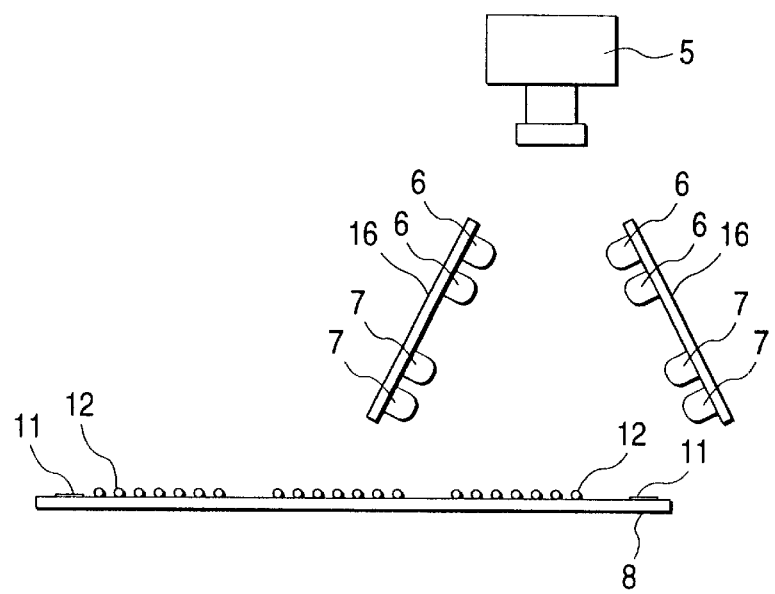
FIG. 3 shows an explanatory diagram showing a relationship between an illuminator and the BGA frame.

Two illuminations, that is, first and second illumination, are provided in the illuminator 16 of the mount inspection portion 3. The first illumination is constituted by continuous illuminations 6 provided in an upper portion of a slope in the illuminator 16 for inspecting the alignment marks 11 of the BGA packages 9. The alignment marks 11 can be easily recognized when they are illuminated from a substantially vertical direction. Therefore, the continuous illuminations 6, which constitute the first illumination, illuminate the alignment marks 11 from a substantially vertical direction. In FIG. 3, the continuous illuminations 6 are provided in two stages in the upper portion of the slope in the illuminator 16 in the substantially vertical direction above the alignment mark 11 of the BGA package 9.

The second illumination is constituted by stroboscopic illuminations 7 provided in a lower portion of the slope in the illuminator 16 so as to inspect balls. If the illumination for inspecting balls is performed from a substantially vertical direction to the balls, images of things other than the solder balls 12 on the BGA package 9 will be also picked up to thereby increase noise. For such a reason, the solder balls 12 can be easily recognized when they are illuminated obliquely. Accordingly, the stroboscopic illuminations 7, which constitute the second illumination, irradiate the solder balls 12 at a certain angle obliquely. In FIG. 3, in the lower portion of the slope in the illuminator 16, the stroboscopic illuminations 7 are provided in two stages obliquely above the solder balls 12 mounted on the BGA package 9. White LEDs are used as illuminants for both the continuous illuminations 6 and stroboscopic illuminations 7. The continuous light and stroboscopic light can be distinguished by a difference between electric circuits for driving those illuminations.

Figure 4:
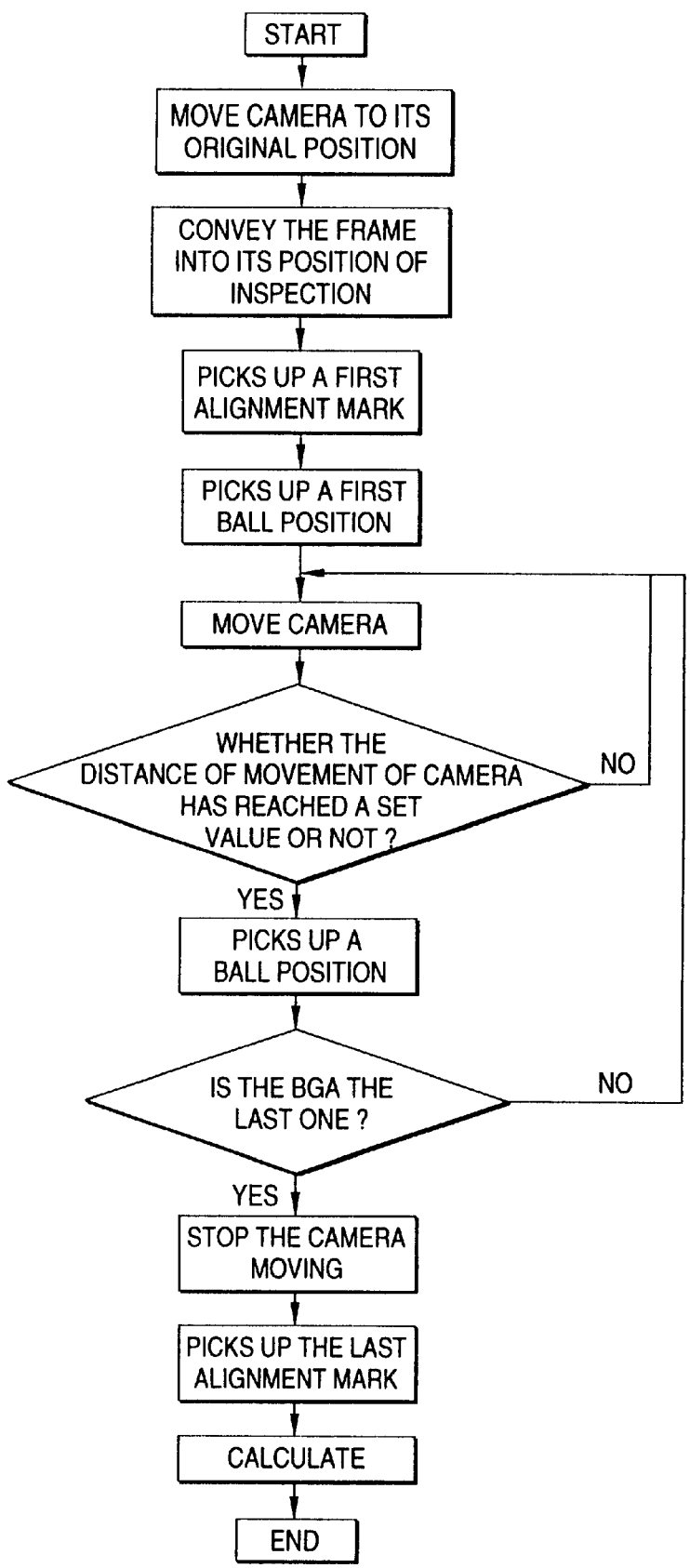
FIG. 4 shows an operation flow chart of a mount inspection apparatus.

Next, description will be made about the procedure of inspection in the mount inspection portion 3. FIG. 4 is an operation flow chart of the mount inspection apparatus. In a first step, the CCD camera 5 moves above a position in an image pick-up area 10 of the first BGA package 9 of the BGA frame 8, that is, moves to a camera original position. The CCD camera 5 stands ready there. In a second step, the BGA frame 8 is conveyed into the mount inspection portion 3 by the conveyor, and then the top BGA package 9 stops in the image pick-up area 10 of the CCD camera 5.

Here, in a third step, an image of the first alignment mark 11 is picked up by the continuous illuminations 6. Successively, in a fourth step, a positional image of the first solder ball 12 is picked up by the stroboscopic illuminations 7. At the same time, as a fifth step, the relative movement between the BGA frame 8 and the CCD camera 5 is started. Specifically, the CCD camera 5 is moved.

In a six step, judgment is made as to whether the movement of the CCD camera 5 has reached a set distance or not, that is, as to whether the second BGA package 9 has arrived in the image pick-up area 10 of the CCD camera 5 or not. If it has arrived (if YES), in a seventh step, the stroboscopic illuminations 7 are turned ON so as to pick up the positional image of the solder balls 12 in the second BGA package 9.

The timing for picking up an image while the CCD camera 5 is being moved is controlled in such a manner that the pitch between the BGA packages 9 is inputted in advance, the motion of the CCD camera 5 is observed by an encoder attached to the camera moving motor 14, and the timing for picking up an image is controlled by the number of pulses generated by the encoder. In an eighth step, judgment is made as to whether the BGA package 9 is the last one or not. If it is not the last one, the positional images of the solder balls 12 on the third and the following BGA packages 9 are picked up in the same manner.

When the positional image of the solder balls 12 on the last BGA package 9 has been picked up and it is concluded that the BGA package 9 is the last one, the CCD camera 5 is stopped moving in a ninth step. The image of the rearmost alignment mark 11 is picked up in a tenth step after the CCD camera 5 has been stopped. After the image has been picked up, in an eleventh step, the inclination of the BGA frame 8 as a whole obtained on the basis of the top and rearmost alignment marks 11 is calculated (to obtain the posture as a whole), the positions of the solder balls 12 on the BGA packages 9 are calculated while taking the inclination (posture) of the BGA frame 8 into consideration, and judgment is made as to whether the positions of the solder balls 12 mounted on the BGA packages 9 are good or bad. The posture of the BGA frame 10 can be calculated in a simple manner using two coordinates of the alignment marks 11.

The present invention has such effects as follows. First, a mount inspection apparatus picks up images of top and rearmost alignment marks, obtains the posture of the work as a whole on the basis of the top and rearmost alignment marks, calculates the positions of balls mounted on BGA packages while taking the posture into consideration, and judges whether the positions of the mounted balls are good or bad. Accordingly, it is not necessary to pick up images of inclinations of the individual packages so that the inspection time is shortened.

Second, in a ball mount inspection apparatus for a work in which a plurality of BGA packages are formed, the top BGA package is stopped in an image pick-up area, an alignment mark image is picked up, successively a ball image is picked up while relative movement between the work and a camera is started, ball images of the second and the following BGA packages are picked up while the relative movement is continued, the relative movement is stopped when a ball image of the last BGA package is picked up, and the rearmost alignment mark image of the rearmost BGA package is picked up after the relative movement is stopped. Accordingly, inspection can be carried out at a high speed in comparison with means which stops at every package.

Although the invention has been described in its preferred form with a certain degree of particularity, it is understood that the present disclosure of the preferred form can be changed in the details of construction and in the combination and arrangement of parts without departing from the spirit and the scope of the invention as hereinafter claimed.

What is claimed is:

1. A mount inspection apparatus for inspecting whether positions of balls mounted on each of a plurality of ball grid array packages being formed on a work are good or not, said apparatus comprising:

conveyor means for conveying the work;

a mount inspection portion disposed above said conveyor means and moving horizontally to pick up images of said balls mounted on said ball grid array packages and images of alignment marks being put at least on top and rearmost ones of said ball grid array packages; and calculating means for calculating a posture of said work based on the images of the alignment marks picked up by said mount inspection portion, to thereby obtain the positions of balls mounted on said ball grid array packages and inspect the positions of mounted balls are good or not.

2. A mount inspection apparatus according to claim 1, wherein said mount inspection portion comprises a camera and an illuminator.

3. A mount inspection apparatus according to claim 2, wherein said illuminator comprises a first illumination for inspecting the alignment marks, and a second illumination for inspecting the balls.

4. A mount inspection apparatus according to claim 3, wherein said first illumination comprises a continuous illumination provided in an upper portion of said illuminator, and said second illumination comprises a stroboscopic illumination provided in a lower portion of said illuminator.

5. A method for inspecting whether positions of balls mounted on each of a plurality of ball grid array packages being formed on a work are good or not, said method comprising steps of:

picking up an image of an alignment mark being put on a top one of said ball grid array packages;

picking up images of the balls mounted on said ball grid array packages;

picking up an image of an alignment mark being put on a rearmost one of said ball grid array packages; and calculating a posture of said work based on the images of the picked-up alignment marks to thereby obtain the positions of balls mounted on said ball grid array packages and inspect the positions of mounted balls are good or not.

6. An inspecting method according to claim 5, further comprising a step of relatively moving the work with respect to means for picking up the images of the alignment marks and the balls.

* * * * *